US012734229B2

(12) United States Patent
Kapre et al.

(10) Patent No.: US 12,734,229 B2
(45) **Date of Patent: *Sep. 15, 2026**

(54) MULTIVALENT PNEUMOCOCCAL GLYCOCONJUGATE VACCINES CONTAINING EMERGING SEROTYPE 24F

(71) Applicant: Inventprise, Inc., Redmond, WA (US)

(72) Inventors: Subhash V. Kapre, Redmond, WA (US); Anup K. Datta, Renton, WA (US)

(73) Assignee: Inventprise, Inc., Redmond, WA (US)

( * ) Notice: Subject to any disclaimer, the term of this patent is extended or adjusted under 35 U.S.C. 154(b) by 210 days.

This patent is subject to a terminal disclaimer.

(21) Appl. No.: 18/777,826

(22) Filed: Jul. 19, 2024

(65) Prior Publication Data

US 2024/0366743 A1 Nov. 7, 2024

Related U.S. Application Data

(63) Continuation of application No. 17/398,231, filed on Aug. 10, 2021, now Pat. No. 12,053,515.

(60) Provisional application No. 63/063,842, filed on Aug. 10, 2020.

(51) Int. Cl.

| | |
|---|---|
| ***A61K 39/09*** | (2006.01) |
| ***A61K 39/116*** | (2006.01) |
| ***A61P 31/04*** | (2006.01) |
| *A61K 39/00* | (2006.01) |

(52) U.S. Cl.

CPC .......... *A61K 39/092* (2013.01); *A61K 39/116* (2013.01); *A61P 31/04* (2018.01); *A61K 2039/6037* (2013.01); *A61K 2039/6068* (2013.01); *A61K 2039/6081* (2013.01)

(58) Field of Classification Search

CPC combination set(s) only.
See application file for complete search history.

(56) References Cited

U.S. PATENT DOCUMENTS

| | | | |
|---|---|---|---|
| 4,673,574 | A | 6/1987 | Anderson |
| 4,686,102 | A | 8/1987 | Ritchey et al. |
| 4,902,506 | A | 2/1990 | Anderson et al. |
| 5,360,897 | A | 11/1994 | Anderson et al. |
| 5,371,197 | A | 12/1994 | Marburg et al. |
| 5,565,204 | A | 10/1996 | Kuo et al. |
| 5,623,057 | A | 4/1997 | Marburg et al. |
| 5,681,570 | A | 10/1997 | Yank et al. |
| 5,807,553 | A | 9/1998 | Malcolm |
| 5,847,112 | A | 12/1998 | Kniskern et al. |
| 5,849,301 | A | 12/1998 | Lees |
| 5,866,132 | A | 2/1999 | Malcolm |
| 5,965,714 | A | 10/1999 | Ryall |
| 6,132,723 | A | 10/2000 | Malcolm |
| 6,177,085 | B1 | 1/2001 | Yank et al. |
| 6,224,880 | B1 | 5/2001 | Chan et al. |
| 6,656,472 | B1 | 12/2003 | Chong et al. |
| 6,863,893 | B2 | 3/2005 | Wizemann et al. |
| 7,018,637 | B2 | 3/2006 | Chong et al. |
| 7,435,421 | B2 | 10/2008 | Wizemann et al. |
| 7,501,132 | B2 | 3/2009 | Ades et al. |
| 7,524,821 | B2 | 4/2009 | Wang et al. |
| 7,709,001 | B2 | 5/2010 | Hausdorff et al. |
| 7,862,823 | B1 | 1/2011 | Leroy |
| 7,955,605 | B2 | 6/2011 | Prasad |
| 8,007,807 | B2 | 8/2011 | Borkowski |
| 8,029,798 | B2 | 10/2011 | Leroy |
| 8,048,432 | B2 | 11/2011 | Lee et al. |
| 8,173,135 | B2 | 5/2012 | Lee |
| 8,226,959 | B2 | 7/2012 | Gibson et al. |
| 8,246,964 | B2 | 8/2012 | Beninati et al. |
| 8,361,477 | B2 | 1/2013 | Borkowski |
| 8,398,985 | B2 | 3/2013 | Kapre |
| 8,444,992 | B2 | 5/2013 | Borkowski |
| 8,465,749 | B2 | 6/2013 | Lee et al. |
| 8,481,054 | B2 | 7/2013 | Nahm et al. |
| 8,557,250 | B2 | 10/2013 | Lee |
| 8,575,319 | B2 | 11/2013 | Timmerman |
| 8,603,484 | B2 | 12/2013 | Prasad |
| 8,642,048 | B2 | 2/2014 | Ades et al. |

(Continued)

FOREIGN PATENT DOCUMENTS

| | | |
|---|---|---|
| WO | WO2017/173415 | 10/2017 |
| WO | WO2018/064444 | 4/2018 |

(Continued)

OTHER PUBLICATIONS

Search Report of EP Application No. 21856548.9 dated Jul. 18, 2024.

(Continued)

*Primary Examiner* — Jennifer E Graser
(74) *Attorney, Agent, or Firm* — Remenick PLLC

(57) ABSTRACT

The invention is directed to multivalent pneumococcal glycoconjugate compositions containing a newly emerging serotype of *S. pneumonia*, polysaccharide 24F, and their manufacture and use. The pneumococcal serotype 24F contains a polysaccharide repeating unit structure. The multivalent immunogenic composition comprises at least 25 *S. pneumonia* capsular polysaccharides selected from the serotypes 1, 2, 3, 4, 5, 6B, 6C, 7F, 8, 9N, 9V, 10A, 11A, 12F, 14, 15A, 15B, 15C, 16F, 17F, 18C, 19A, 19F, 20, 22F, 23B, 23F, 24F, 33F and 35B of *S. pneumoniae* preferably conjugated to carrier protein either directly or through a linker and a pharmaceutically acceptable carrier and/or adjuvant. The disclosure provides the capsular polysaccharide structure of serotype 24F to understand the polysaccharide before conjugation with carrier protein.

40 Claims, 3 Drawing Sheets

(56) References Cited

U.S. PATENT DOCUMENTS 8,652,480 B2 2/2014 Yuan et al.
8,703,148 B2 4/2014 Biemans et al.
8,753,649 B2 6/2014 Lee et al.
8,784,826 B2 7/2014 Borkowski
8,795,689 B2 8/2014 Crinean
8,808,707 B1 8/2014 Siber et al.
8,808,708 B2 8/2014 Hausdorff et al.
8,815,254 B2 8/2014 Biemans et al.
8,895,024 B2 11/2014 Hausdorff et al.
8,933,218 B2 1/2015 Biemans et al.
8,999,697 B2 4/2015 Yuan et al.
9,095,567 B2 8/2015 Khandke et al.
9,107,872 B2 8/2015 Biemans et al.
9,173,931 B2 11/2015 Jessouroun et al.
9,175,033 B2 11/2015 Lee
9,198,976 B2 12/2015 Lee et al.
9,198,977 B2 12/2015 Kapre
9,205,143 B2 12/2015 Davis et al.
9,283,270 B2 3/2016 Kapre
9,399,060 B2 7/2016 Hausdorff et al.
9,474,795 B2 10/2016 Lee et al.
9,475,804 B2 10/2016 Wightman
9,480,736 B2 11/2016 Hausdorff et al.
9,492,559 B2 11/2016 Emini et al.
9,499,593 B2 11/2016 Malley et al.
9,517,274 B2 12/2016 Gu et al.
9,610,339 B2 4/2017 Biemans et al.
9,610,340 B2 4/2017 Biemans et al.
9,669,084 B2 6/2017 Siber et al.
9,675,681 B2 6/2017 Yuan et al.
9,778,266 B2 10/2017 Nahm et al.
9,884,113 B2 2/2018 Biemans et al.
9,902,724 B2 2/2018 Wightman
9,950,054 B2 4/2018 Gu et al.
9,981,035 B2 5/2018 Hausdorff et al.
9,981,045 B2 5/2018 Prasad
10,159,728 B2 12/2018 Kapre
10,688,170 B2 6/2020 Kapre
10,729,763 B2 8/2020 Kapre
2001/0048929 A1 12/2001 Chong et al.
2002/0094338 A1 7/2002 Jonsdottir
2003/0099672 A1 5/2003 Schultz
2003/0138447 A1 7/2003 Wizemann et al.
2003/0147922 A1 8/2003 Capiau et al.
2005/0118199 A1 6/2005 Esser et al.
2005/0142145 A1 6/2005 Wizemann et al.
2005/0159341 A1 7/2005 Wang et al.
2005/0214329 A1 9/2005 Laferriere et al.
2005/0226891 A1 10/2005 Ades et al.
2006/0051361 A1 3/2006 Laferriere et al.
2006/0093626 A1 5/2006 Capiau et al.
2006/0140981 A1 6/2006 Jonsdottir
2006/0228380 A1 10/2006 Hausdorff et al.
2007/0110762 A1 5/2007 Jessouroun et al.
2007/0141084 A1 6/2007 Lee et al.
2007/0184071 A1 8/2007 Hausdorff et al.
2007/0184072 A1 8/2007 Hausdorff et al.
2007/0231340 A1 10/2007 Hausdorff et al.
2007/0253985 A1 11/2007 Look et al.
2008/0286838 A1 11/2008 Yuan et al.
2009/0017060 A1 1/2009 Timmerman
2009/0092632 A1 4/2009 Lee
2009/0130137 A1 5/2009 Hausdorff et al.
2009/0136548 A1 5/2009 Ades et al.
2010/0034847 A1 2/2010 Borkowski
2010/0074922 A1 3/2010 Biemans et al.
2010/0143414 A1 6/2010 Nahm et al.
2010/0158953 A1 6/2010 Crinean
2010/0183662 A1 7/2010 Biemans et al.
2010/0209450 A1 8/2010 Biemans et al.
2010/0239604 A1 9/2010 Biemans et al.
2010/0303852 A1 12/2010 Biemans et al.
2010/0316666 A1 12/2010 Hausdorff et al.
2010/0322959 A1 12/2010 Biemans et al.
2011/0071279 A1 3/2011 Hausdorff et al.
2011/0076301 A1 3/2011 Beninati et al.
2011/0091506 A1 4/2011 Gibson et al.
2011/0117123 A1 5/2011 Leroy
2011/0159030 A1 6/2011 O'Hagan
2011/0195086 A1 8/2011 Caulfield
2011/0201791 A1 8/2011 Prasad
2011/0311574 A1 12/2011 Borkowski
2012/0076817 A1 3/2012 Lee et al.
2012/0135037 A1 5/2012 Mizel et al.
2012/0195922 A1 8/2012 Lee
2012/0231086 A1 9/2012 Killen et al.
2012/0237542 A1 9/2012 Hausdorff et al.
2012/0321658 A1 12/2012 Biemans et al.
2013/0004535 A1 1/2013 Borkowski
2013/0004536 A1 1/2013 Borkowski
2013/0072881 A1 3/2013 Khandke et al.
2013/0315958 A1 11/2013 Nahm et al.
2013/0337004 A1 12/2013 Lee et al.
2014/0010843 A1 1/2014 Biemans et al.
2014/0044748 A1 2/2014 Lee
2014/0099337 A1 4/2014 Davis et al.
2014/0154286 A1 6/2014 Malley et al.
2014/0227317 A1 8/2014 Wightman
2014/0314805 A1 10/2014 Hausdorff et al.
2014/0322258 A1 10/2014 Lee et al.
2014/0322263 A1 10/2014 Siber et al.
2014/0348868 A1 11/2014 Donati et al.
2014/0363463 A1 12/2014 Yuan et al.
2015/0038685 A1 2/2015 Hausdorff et al.
2015/0079132 A1 3/2015 Maisonneuve et al.
2015/0165017 A1 6/2015 Yuan et al.
2015/0165019 A1 6/2015 Del Giudice
2015/0202309 A1 7/2015 Emini et al.
2015/0216996 A1 8/2015 Gu et al.
2015/0231270 A1 8/2015 Prasad
2015/0265702 A1 9/2015 Biemans et al.
2015/0328328 A1 11/2015 Han et al.
2015/0344530 A1 12/2015 Kapre
2016/0136256 A1 5/2016 Lee et al.
2016/0158345 A1 6/2016 Hausdorff et al.
2016/0324948 A1 11/2016 Gu et al.
2016/0324949 A1 11/2016 Han et al.
2017/0021006 A1 1/2017 Watson et al.
2017/0021008 A1 1/2017 Drew
2017/0037045 A1 2/2017 Wightman
2017/0143821 A1 5/2017 Porro
2017/0224804 A1 8/2017 Gu et al.
2017/0246313 A1 8/2017 Gill et al.
2017/0252423 A1 9/2017 Siber et al.
2018/0136224 A1 5/2018 Nahm et al.
2018/0186792 A1 7/2018 Wightman
2018/0221467 A1 8/2018 Gu et al.
2018/0250390 A1 9/2018 Hausdorff et al.
2018/0256739 A1 9/2018 Prasad
2018/0353591 A1 12/2018 Kapre et al.
2019/0000953 A1 1/2019 Gu et al.
2020/0030439 A1 1/2020 Kapre
2021/0220461 A1 7/2021 Kapre

FOREIGN PATENT DOCUMENTS

WO WO2018/227177 12/2018
WO WO2019/050815 3/2019
WO WO2019/139692 7/2019
WO WO2020/009993 1/2020
WO WO2021/021729 2/2021
WO WO2021/146681 7/2021

OTHER PUBLICATIONS

Examination Report of EP Application No. 21856548.9 dated Jul. 18, 2024.
Examination Report of JP Application No. 2023-509513 dated Jul. 23, 2024.
Examination Report of JP Application No. 2023-509513 dated Jul. 23, 2024 (translated).
Search Report and Written Opinion for WIPO Application No. PCT/US2021/45334 dated Nov. 22, 2021.

(56) References Cited

OTHER PUBLICATIONS

Examination Report of JP Application No. 2023-509513 dated Mar. 5, 2024.

Examination Report of JP Application No. 2023-509513 dated Mar. 5, 2024 (translated).

| SEROTYPE | 1 | 3 | 4 | 5 | 6B | 7F | 9V | 14 | 18C | 19A | 19F | 23F | |
|---|---|---|---|---|---|---|---|---|---|---|---|---|---|
| IVT - PCV - 25V | 13.34 | 2.55 | 4.76 | 6.52 | 15.01 | 45.23 | 10.17 | 46.70 | 16.04 | 7.69 | 18.63 | 9.52 | |
| PREVNAR - 13 | 2.63 | 1.69 | 5.03 | 3.62 | 18.13 | 9.71 | 4.66 | 4.45 | 9.51 | 7.02 | 20.51 | 8.08 | |
| | | | | | | | | | | | | | |
| | 2 | 6C | 8 | 9N | 10A | 12F | 15A | 15B | 16F | 22F | **24F** | 33F | 35B |
| IVT - PCV - 25V | 21.57 | 22.32 | 20.24 | 59.78 | 10.56 | 3.91 | 40.85 | 16.37 | 229.20 | 38.72 | **70.63** | 23.75 | 48.75 |

MULTIVALENT PNEUMOCOCCAL GLYCOCONJUGATE VACCINES CONTAINING EMERGING SEROTYPE 24F

REFERENCE TO RELATED APPLICATIONS

This application is a continuation of U.S. application Ser. No. 17/398,231, filed Aug. 10, 2021, which issued as U.S. Pat. No. 12,053,515 on Aug. 6, 2024, which claims priority to U.S. Provisional Application No. 63/063,842 filed Aug. 10, 2020, the entirety of each of which is incorporated herein.

BACKGROUND

1. Field of the Invention

This invention is directed to composition containing immunogenic components of *Streptococcus pneumoniae* serotype 24F, and methods for the manufacture of immunogenic compositions and method for the prevention of *S. pneumoniae* infection and/or treatments of patients infected with *S. pneumoniae.*

2. Description of the Background

*Streptococcus pneumoniae* also referred to as pneumococcus is a Gram-positive pathogen responsible for invasive pneumococcal diseases (IPDs) such as pneumonia, bacteremia, meningitis, and acute Otitis media. Pneumonia is the most common manifestation of invasive pneumococcal disease, whereas bacterial spread within the respiratory tract may result in middle-ear infection, sinusitis or recurrent bronchitis. Pneumococcus is encapsulated with a chemically linked polysaccharide which results in serotype specificity. At least 90 pneumococcal serotypes are known of which about 23 account for 90% of invasive diseases and capsular polysaccharide is a poor immunogen.

There are currently three PCV vaccines available on the global market: PREVNAR®, SYNFLORIX®, and PREVNAR-13®. There is a need to address remaining unmet medical need for coverage of pneumococcal disease due to serotypes not found in PREVNAR-13® and potential for serotype replacement over time. here is a need for immunogenic compositions covering pathogenic serotypes and methodology that can be used to induce a uniform and high immune response against all serotypes including the additional *Streptococcus pneumoniae* serotypes in humans and in children less than two years old.

A capsular polysaccharide (CPS) is a key virulence determinant and generally insufficiently immunogenic to induce a T cell-dependent immune response in infants and children. Conjugation of a carrier protein to CPS can induce an immune response that undergoes class switching. Accordingly, a 7-valent (PCV-7, Pfizer Inc., USA), a 10-valent (Synflorox-10, GSK Vaccines) and a 13-valent pneumococcal conjugate vaccine (PCV-13, Pfizer Inc., USA) have been developed to efficiently prevent the incidence of IPDs. Reductive amination chemistry and cyanylation chemistry has been widely used to prepare the conjugate vaccines.

U.S. Pat. No. 9,492,559 discloses immunogenic compositions comprising conjugated capsular polysaccharide antigens and uses thereof. The immunogenic compositions disclosed include an 8, 9, 10, 11, 12, 13, 14, 15, 16, 17, 18, 19 or 20-valent pneumococcal conjugate composition. Also disclosed is a 7, 8, 9, 10, 11, 12, 13, 14, 15, 16, 17, 18, 19, 20, 21, 22, 23, 24 or 25-valent pneumococcal conjugate composition.

International Application Publication No. WO 2014/097099A2 discloses a glycol-conjugation process directed to several serotypes in addition to Preevnar-13 valent conjugates. New polysaccharide conjugates are added to formulation to increase efficacy of the vaccine.

U.S. Patent Application Publication No. 2011/023526 discloses a 15-valent pneumococcal polysaccharide-protein conjugate vaccine composition. This patent is directed to 15-valent conjugate vaccines made by adding two or more serotypes with currently available 1-3 vaccines.

International Application Publication No. WO 2016/207905 discloses multivalent pneumococcal conjugate vaccine. This application is directed to a 13 or greater valent conjugate vaccine and deletion of serotype 6A.

U.S. Patent Application Publication No. 2017/007713 discloses a linker containing ((2-oxoethyl) thio) with enhanced functionality.

International Application Publication No. WO 2014/092377 discloses a 13 valent composition wherein 12 serotypes were selected from the group consisting of serotypes 1, 3, 4, 5, 6A, 6B, 7F, 9V, 14, 18C, 19A, 19F, and 23F and one from 12 or 9N.

International Application Publication No. WO 2014/092378 discloses an immunogenic composition having 13 different polysaccharide-protein conjugates wherein each conjugate contained a capsular polysaccharide isolated from 12 serotypes selected from the group consisting of serotypes 1, 3, 4, 5, 6A, 6B, 7F, 9V, 14, 18C, 19A, 19F and 23F, and serotypes 22F or 33F.

Chinese Application Publication No. 101590224 discloses a 14-valent pneumococcal polysaccharide-protein conjugate vaccine containing serotypes 1, 2, 4, 5, 6A, 6B, 7F, 9N, 9V, 14, 18C, 19A, 19F and 23F.

Chinese Application Publication No. 104069488 discloses 14 valent polysaccharide protein conjugate wherein the 14 serotypes were 1, 4, 5, 6A, 6B, 7F, 9V, 14, 18C, 19A, 19F, 22F, 23F and 33F.

International Application Publication No. WO 2016207905 discloses a multivalent pneumococcal conjugate vaccine comprising conjugates of CRM197 and at least 14 capsular polysaccharides selected from serotypes 1, 3, 4, 5, 6B, 7F, 9N, 9V, 14, 15B, 18C, 19A, 19F, 22F, 23F and 33F. U.S. Pat. No. 8,192,746 disclosed a 15 valent immunogenic composition comprising capsular polysaccharides from serotypes 1, 3, 4, 5, 6A, 6B, 7F, 9V, 14, 18C, 19A, 19F, 22F, 23F, and 33F conjugated to CRM197.

International Application Publication No. WO 2013/191459 discloses a 15 valent composition comprising *S. pneumoniae* capsular polysaccharides form serotypes of 1, 2, 3, 4, 5, 6A, 6B, 7F, 9N, 9V, 14, 18C, 19A, 19F and 23F.

Chinese Application Publication No. 103656632 discloses multi valent pneumococcal capsular polysaccharide composition containing serotype 6A and at least one extra serotype selected from the group consisting of 1, 2, 3, 4, 5, 6B, 7F, 8, 9N, 10A, 11A, 12F, 14, 15B, 17F, 18C, 19A, 19F, 20, 22F, 23F and 33F which provided protection against 24 different pneumococci serotypes.

Chinese Application Publication No. 103656631 discloses a multivalent pneumococcus capsular polysaccharide-protein conjugate composition comprising capsular polysaccharides of pneumococcus of 24 different serotypes viz. 1, 2, 3, 4, 5, 6A, 6B, 7F, 8, 9N, 9V, 10A, 11A, 12F, 14, 15B, 17F, 18C, 19A, 19F, 20, 22F, 23F and 33F.

U.S. Patent Application Publication No. 2016/0324950 discloses immunogenic polysaccharide-protein conjugates comprising a capsular polysaccharide (CP) from *Streptococcus agalactiae*, also referred to as group B streptococcus (GBS), and a carrier protein, wherein the CP is selected from the group consisting of serotypes Ia, Ib, II, III, IV, V, VI, VII, VIII, and IX. This was meant for treatment of chronic diabetes mellitus, cancer, heart failure, neurologic, and urologic conditions. The carrier protein capsular polysaccharide conjugates varied.

U.S. Pat. No. 5,360,897 discloses immunogenic conjugate comprising reductive amination product of an intact capsular polymer of the bacterial pathogen *S. pneumoniae* having at least two carbonyl groups and a bacterial toxin or toxoid, said conjugate comprising a cross-linked conjugate in which there is a direct covalent linkage between the capsular polymer and the toxin or toxoid.

U.S. Pat. No. 7,862,823 describes a multivalent conjugate vaccine composition with at least two different carrier proteins.

U.S. Pat. No. 8,808,708 discloses a 13-valent immunogenic composition consisting of polysaccharide-protein conjugates where serotypes consist of 1, 3, 4, 5, 6A, 6B, 7F, 9V, 14, 18C, 19A, 19F and 23F, and wherein the carrier protein is CRMI97.

U.S. Patent Application Publication No. 2009/0017059 discloses an immunogenic composition where serotypes 19A and 19F were conjugated to different bacterial toxoids.

International Application Publication No. WO 2011/110241 describes pneumococcal conjugate immunogenic compositions or vaccines wherein different conjugation chemistries were used for different components of the immunogenic composition or vaccine. Reductive amination was used for the conjugation of at least one serotype and a conjugation other than reductive amination was used for the conjugation of a different serotypes. The conjugation method selected for different serotypes allowed each serotype to be presented using a conjugation method that allowed the best presentation of the saccharide epitope. Some pneumococcal saccharides conjugated well using reductive amination, whereas other pneumococcal saccharides were conjugated differently to allow the ring structure to remain unbroken and provide better results.

U.S. Pat. No. 7,955,605 discloses a process of making carrier protein polysaccharide conjugate consisting of serotype 19A where the activated serotype 19A polysaccharide and carrier protein are suspended in dimethyl sulfoxide (DMSO) to form a conjugate.

U.S. Patent Application Publication No. 2010/0074922 discloses immunogenic composition containing 10 or more serotypes wherein 19F capsular saccharide was conjugated to diphtheria toxoid (DT), serotype 18C capsular saccharide is conjugated to tetanus toxoid and serotypes 1, 4, 5, 6B, 7F, 9V, 14 and 23F capsular saccharides are conjugated to Protein D from *Haemophilus influenza.*

U.S. Patent Application Publication No. 2010/0239604 discloses a composition comprising multivalent *S. pneumoniae* capsular saccharide conjugates wherein serotype 19A was conjugated to a first bacterial toxoid and 19F is conjugated to a second bacterial toxoid and 2-9 of the *S. pneumoniae* capsular saccharides are conjugated to protein D. Apart from increasing the scope of protection by developing vaccines which will offer protection against larger number of serotypes, efforts were focused on developing newer methods of synthesis.

U.S. Pat. No. 7,709,001 describes a method of synthesis of carrier protein conjugate of capsular polysaccharide which consists of 1) reacting purified polysaccharide with a mild acid resulting in size reduction 2) reacting the polysaccharide of step 1 with an oxidizing agent in the presence of bivalent cations resulting in an activated polysaccharide; 3) compounding the activated polysaccharide with a carrier protein 4) reacting activated polysaccharide of step 3 and carrier protein with a reducing agent to form a polysaccharide—carrier protein conjugate; and 5) capping unreacted aldehydes in product of step 4 to yield an immunogenic polysaccharide-carrier protein conjugate.

International Application Publication No. WO 2014/097099 discloses a method of synthesizing a carrier protein conjugate, which involves a) reacting a saccharide with 2,2,6,6-tetramethyl-1-piperidinyloxy (TEMPO) and N-chlorosuccinimide (NCS) in an aqueous solvent to produce an activated saccharide; and b) reacting the activated saccharide with a carrier protein comprising one or more amine groups.

U.S. Patent Application Publication No. 2012/321658 discloses an immunogenic composition wherein serotypes 1, 3, 19A and 19F linked to protein carriers either directly or indirectly through a chemistry other than reductive amination, and one or more different saccharides is/are selected from a second group consisting of serotypes 4, 5, 6A, 6B, 7F, 9V, 14, 18C and 23F which is/are linked to a protein carriers) by reductive amination.

Pneumococcal vaccines are based on 1) pneumococcal polysaccharide vaccine and 2) pneumococcal conjugate vaccines. PNEUMOVAX® marketed by Merck comprises of unconjugated polysaccharides belonging to serotypes 1, 2, 3, 4, 5, 6B, 7F, 8, 9N, 9V, 10A, 11A, 12F, 14, 15B, 17F, 18e, 19F, 19A, 20, 22F, 23F and 33F. Infants and young children respond poorly to most pneumococcal polysaccharides. Immunogenicity of poor immunogens is enhanced by conjugating with carrier proteins. Polysaccharide protein conjugate vaccines are made using capsular polysaccharides linked to protein carriers. The conjugate induces T cell dependent enhanced immune response against the specific serotype.

Conjugates are synthesized using various reagents, such as homo bifunctional, hetero bifunctional spacers and linkers of varying lengths. Three pneumococcal conjugate vaccines are available in market, PREVNAR®, SYNFLORIX®, and PREVNAR-13®. PREVNAR® is a heptavalent vaccine that contains the capsular polysaccharides from serotypes 4, 6B, 9Y, 14, 18C, 19F and 23F, each conjugated to a carrier protein designated CRM197. SYNFLORIX® is a deca-valent vaccine from GSK Biologicals that incorporates ten capsular polysaccharides conjugated to protein D from NTHi offering coverage against three additional pneumococcal strains, serotypes 1, 5 and 7F. PREVNAR-13® is a tri-deca-valent vaccine containing 13 capsular polysaccharide prepared from thirteen serotype of *Streptococcus pneumoniae* (1, 3, 4, 5, 6A, 6B, 7F, 9Y, 14, 18C, 19 A, 19F, and 23F) conjugated to a carrier protein designated CRM197.

Increasing microbial resistance to antibiotics and the increasing number of immunocompromised persons have necessitated the development of pneumococcal vaccines with even broader protection, which leads to development of multivalent vaccines effective against increasing number of serotypes especially for coverage of pneumococcal disease due to serotypes not found in PREVNAR-13®. The need for a specific serotype depends on the region and antibiotic resistance developed. Thus, U.S. Pat. No. 8,192,746 reports a multivalent immunogenic composition having 15 distinct polysaccharide-protein conjugates. Each conjugate consists of a capsular polysaccharide prepared from serotype of

*Streptococcus pneumoniae* (1, 3, 4, 5, 6A, 6B, 7F, 9\1, 14, 18C, 19A, 19F, 22F, 23F, or 33F) conjugated to a carrier protein CRM197. There is a need for vaccines that induce an immune response against serotype 15B, 15C, and 15A.

With the current methods increasing number of polysaccharide antigens in the multivalent conjugate vaccine formulations, the carrier protein content increases. This increase leads to an increase of immune response to the carrier protein which can cause a systemic overload. This needs to be reduced. Also, there is a lowering of immune response as the serotypes increase, which needs to be increased.

Thus, there is a need to develop a pneumococcal vaccine that provides uniform protection against increasing number of serotypes, and a reduction of the immune response to the carrier protein and especially newly characterized serotype 24F. Also, the immune response to individual serotypes is preferably not affected by an increase in the antigen number. In the development of multivalent vaccines that extend the immune stimulus for existing and additional serotypes, there is a need to work on all factors involved in the conventional established conjugation methods. In addition to offering suitable protection against increasing number of serotypes, there is also a need to develop methods to reduce carrier protein antibodies in spite of an increase in the number of serotypes.

SUMMARY OF THE INVENTION

The present invention overcomes the problems and disadvantages associated with current strategies and designs and provides new compositions, tools and methods for the prevention of *S. pneumoniae* infection and/or treating patients infected with *S. pneumoniae*.

One embodiment of the invention is directed to multivalent immunogenic compositions containing at least 25 capsular polysaccharides of *S. pneumonia* selected from serotypes 1, 2, 3, 4, 5, 6B, 6C, 7F, 8, 9N, 9V, 10A, 11A, 12F, 14, 15A, 15B, 15C, 16F, 17F, 18C, 19A, 19F, 20, 22F, 23B, 23F, 24F, 33F and 35B. Immunogenic compositions preferably contain serotype 24F which preferably contains chemical structure with an established repeating unit of the 24F polysaccharide. Preferably the polysaccharides are conjugated to carrier proteins directly or through a linker molecule. Linker are preferably bivalent or multivalent linkers.

Another embodiment of the invention is directed to vaccines comprising the immunogenic compositions disclosed herein.

Another embodiment of the invention is directed to methods for the manufacture of the immunogenic compositions disclosed herein.

Another embodiment of the invention is directed to methods for the prevention and/or treatment of *S. pneumonia* infections comprising administering the immunogenic compositions disclosed herein to a subject. Preferably the subject is a mammal.

Other embodiments and advantages of the invention are set forth in part in the description, which follows, and in part, may be obvious from this description, or may be learned from the practice of the invention.

DESCRIPTION OF THE INVENTION

As embodied and broadly described herein, the present invention is directed to new compositions, tools and methods for the prevention of *S. pneumoniae* infection and/or treating patients infected with *S. pneumoniae*.

Figure 1:
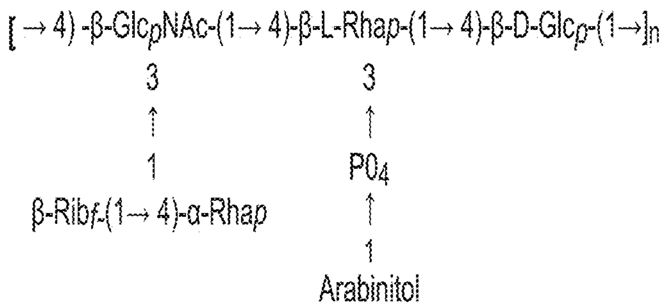
FIG. 1 Chemical structure of native *S. Pneumoniae* 24F Capsular Polysaccharide.

The disclosure is directed to an immunogenic multivalent serotype composition comprising a conjugated pneumococcal immunogenic composition comprising at least 25 pneumococcal polysaccharide serotypes which are individually conjugated to a pharmaceutically acceptable carrier protein, such as for example, CRM197, wherein the composition contains capsular polysaccharide from serotype 24F. Preferably the serotype 24F capsular polysaccharide has the chemical structure disclosed in FIG. 1.

The disclosure is also directed to an immunogenic multivalent serotype composition wherein the capsular polysaccharides are obtained or derived from serotypes 1, 2, 3, 4, 5, 6B, 6C, 7F, 8, 9N, 9V, 10A, 12F, 14, 15A, 15B, 16F, 18C, 19A, 19F, 22F, 23F, 24F, 33F and 35B of *S. pneumoniae* conjugated to a carrier protein. Preferred carrier proteins include, for example, native or recombinant cross-reactive material (CRM) or a domain of CRM, CRM197, tetanus toxin, tetanus toxin heavy chain proteins, diphtheria toxoid, tetanus toxoid, *Pseudomonas* exoprotein A, *Pseudomonas aeruginosa* toxoid, *Bordetella pertusis* toxoid, *Clostridium perfringens* toxoid, *Escherichia coli* heat-labile toxin B subunit, *Neisseria meningitidis* outer membrane complex, *Hemophilus influenzae* protein D, Flagellin Fli C, Horseshoe crab Haemocyanin, and fragments, derivatives, and modifications thereof. The multivalent immunogenic composition also preferably contains one or more additional serotypes selected from 11A, 15C, I7F, 20 and 23B of *S. pneumoniae*.

The capsular polysaccharide structure of the 24F serotype may be activated for conjugation purpose. Serotype 24F polysaccharide may be isolated after fermentation of microorganisms followed by purification using sequential lytic enzyme treatments, followed by ultra and dia-filtration, and final purification using ion exchange and hydrophobic interaction chromatography (e.g., see U.S. Pat. No. 10,435,433, which is specifically incorporated by reference).

Purified polysaccharide can be characterized by NMR spectroscopy (see FIG. 1), which conforms to the standard 24F polysaccharide obtained elsewhere. Chemical composition analysis of the polysaccharide by High-Performance Anion Exchange—Pulse Amperometry Detection (HPAE-PAD) and by Gas-Liquid chromatography-Mass Spectroscopy (GC-MS) reveals that the polysaccharide composed of L-rhamnose, Arabinitol, N-acetyl-D-glucosamine, D-ribofuranose and D-glucose in about equimolar ratio (i.e., Rhap:GlcpNAc:Glcp:Ribf:Ara), as further described in the examples.

The polysaccharide can be size reduced by physical or chemical processes such as, for example, high pressure homogenization or acid hydrolysis. Size reduction can be for conjugation and/or other purposes. Preferably one or more of the capsular polysaccharides are from about 10 kDa to about 50 kDa, or from about 30 KDa to about 100 KDa, or from about 100 KDa to about 300 KDa. Polysaccharide can be activated and conjugated with carrier proteins either directly or through a bi-functional spacers and linker attached to carrier protein. Suitable linkers/spacers include, for example, the spacer arm comprised of a hetero- or homo-bifunctional or multifunctional spacer arm, such as, for example, $NH_2$-PEG-$NH_2$/NHS, NHS/$NH_2$-PEG-COOH, Mal-PEG-$NH_2$, Mal-PEG-NHS, CHO-PEG-CHO, SH-PEG-$NH_2$, ADH, HZ-PEG-HZ, SMPH, SMCC, 4-Arm-PEG-$NH_2$. Conjugation process details described in Example 2. Preferably the immunogenic composition contains a reduced amount of carrier protein than as compared to an immunogenic composition containing a carrier protein for each polysaccharide, in other words without bi-functional and/or multi-functional linkers (e.g., see U.S. Pat. No. 10,729,763; specifically incorporated by reference). Preferably the carrier protein comprises about equal amount by weight of capsular polysaccharides to total carrier protein. Also preferably, carrier protein may comprise from about 0.5% to about 0.7%, by weight, of the composition.

In another embodiment, the conjugation method involves activation of the saccharide with CDAP to form a cyanate ester. Similarly, carrier protein can be derivatized with a PEGylated Hydrazide or any other bi-functional group containing linker using EDC/sNHS chemistry. The activated saccharide can be coupled via a spacer (linker) group to a preferably hydrazide group on the carrier protein. Preferably, the polysaccharide cyanate ester is coupled with PEGylated hydrazide (HZ-PEG-HZ)) to the carrier protein using carbodiimide (e.g., EDAC or EDC) chemistry via a Hydrazide group on the protein carrier.

Similarly, polysaccharide can be oxidized to create -aldehyde (—CHO) or carboxylic acid (—COOH) group, and then conjugated with carrier protein either directly or through a linker using reductive amination or EDC/sNHS chemistry.

After conjugation of the capsular polysaccharide to the carrier protein, the polysaccharide-protein conjugates can be purified (e.g., enriched with respect to the amount of polysaccharide-protein conjugate) by a concentration/diafiltration operations, and depth filtration. After the individual glycoconjugates are purified, they can be compounded to formulate the immunogenic composition of the disclosure, which can be used as a vaccine.

Preferably the immunogenic composition is a vaccine for the treatment and/or prevention of a Pneumococcus infection. Vaccines may contain adjuvants such as, for example, aluminum salt, calcium phosphate, a liposome of monophosphoryl lipid A (MPLA), saponin QS-21, a TLR7/8 agonist, and derivatives and combinations thereof. Aluminum salt derivatives include, for example, aluminum phosphate, aluminum sulfate and aluminum hydroxide.

In a preferred embodiment, the invention provides a multivalent Pneumococcal conjugate immunogenic composition or vaccine (PCV) composition. Preferably, the disclosure provides 25 valent, 26 valent, 27 valent, 28 valent, 29 valent, 30 valent and greater than 30 valent immunogenic compositions, wherein the composition contains capsular polysaccharide from serotype 24F. Preferred immunogenic compositions comprise capsular polysaccharides selected from 25 or more of serotypes 1, 2, 3, 4, 5, 6B, 6C, 7F, 8, 9N, 9V, 10A, 11A 12F, 14, 15 A, 15B, 15C, 16F, 17F, 18C, 19A, 19F, 20, 22F, 23B, 23F, 24F, 33F and 35B of *S. pneumoniae* conjugated to a carrier protein. Preferably, the amount of polysaccharide from each of the serotypes of *S. pneumoniae* is conjugated to a carrier protein at 2.2 μg each, except for serotype 6B, which involves 4.4 μg.

A compositions of the disclosure may be manufactured according to conventional procedures, such as, for example, as described in U.S. Pat. No. 10,702,596 and WIPO Application Publication No. WO/2020/102791 (each specifically incorporated by reference). In particular, compositions may be formulated with a pharmaceutically acceptable carriers and diluents or vehicle, such as, for example, water or a saline solution. Other pharmaceutically acceptable carriers include, for example, oil, water, water-in-oil or oil-in-water mixtures, an alcohol, a buffer, a mono-, di- or poly-saccharide, a sugar alcohol, a glycerol, or a combination thereof. The composition may contain ingredients such as a buffer, an amino acid such as, for example, histidine, arginine, a preservative, or a stabilizer, polysorbate, an adjuvant such as an aluminum phosphate, and/or a lyophilization excipient.

The compositions of the disclosure can be formulated in a form of a unit single dose vial, multiple dose vial, or pre-filled syringe. The composition may further comprise of preservative 2-phenoxyethanol and the like in multidose formulation. The amount of preservative preferably ranges in amount from 4 to 20 mg/mL.

The compositions of the disclosure may be administered by any conventional route which is used in the field of vaccines, in particular by the systemic, such as parenteral route, e.g. by the subcutaneous, intramuscular, intradermal or intravenous route. An effective amount of the composition comprises a dose needed to elicit antibodies that significantly reduce the likelihood or severity of infectivity of *S. pneumoniae* during a subsequent challenge.

The compositions of the disclosure may further be provided as an immunogenic composition administered as a single 0.5 mL dose formulated to contain: 2.2 μg of each polysaccharide except for 6B about 4.4 μg; about 50-90 μg of CRM197 total carrier protein; 0.2 mg to 1 mg of aluminum phosphate adjuvant; sodium chloride, histidine and buffer as excipients.

The compositions of the disclosure may further contain a serotype composition for formulating a 25, 26, 27, 28, 29, 30 or greater valent PCV comprising: conjugation of the pneumococcal capsular polysaccharides of known size belonging to polysaccharide serotypes activated and individually conjugated to an immunogenic carrier protein either directly or through a bi-functional linker; diafiltration of the individual monovalent pneumococcal conjugates; analysis of the conjugates by SEC-HPLC containing monovalent pneumococcal conjugates before filter sterilization using 0.2 μm filter; and formulation of the 25-valent PCV using 25 monovalent pneumococcal conjugates, wherein about 4.4 μg for serotype 6B, about 2.2 μg for rest of the serotypes, and Adju-Phos® adjuvant together with appropriate excipient and buffer followed by aseptic filling. The serotype composition of the resulting PCV 25 contains serotypes 1, 2, 3, 4, 5, 6B, 6C, 7F, 8, 9V, 9N, 10A, 12F, 14, 15A, 15B, 16F, 18C, 19A, 19F, 22F, 23F, 24F, 33F and 35 B.

The disclosure includes a serotype composition for formulating a 25 valent PCV comprising: PCV 26, 27, 28, 29, 30 or greater valent containing capsular polysaccharide serotypes 1, 2, 3, 4, 5, 6B, 6C, 7F, 8, 9V, 9N, 10A, 12F, 14, 15A, 15B, 16F, 18C, 19A, 19F, 22F, 23F, 24F, 33F and 35B; which may additionally contain one or more capsular polysaccharide serotypes selected from 11A, 15C, I7F, 20 and/or 23B of *S. pneumoniae*.

Carrier proteins are preferably proteins that are non-toxic and non-reactogenic and obtainable in sufficient amount and purity. A carrier protein can be conjugated or joined with a *S. pneumoniae* polysaccharide to enhance immunogenicity of the polysaccharide. Carrier proteins are preferably amenable to standard conjugation procedures. CRM197 including recombinantly manufactured CRM197 in *E. coli* host can be used as the carrier protein. Preferably each capsular polysaccharide is conjugated to a single carrier protein through a PEGylated hydrazide linker. Alternatively, capsular polysaccharides from *S. pneumoniae* may be conjugated to one or more carrier proteins such as inactivated bacterial toxins such as tetanus toxoid (TT), TTHc fragment, pertussis toxoid (PT), *Neisseria* outer membrane proteins such as outer membrane complex C (OMPC), *Neisseria* porins (Por A, PorB), pneumolysin (PLY), pneumococcal surface protein A (PspA), pneumococcal adhesin protein (PsaA), or *Haemophilus influenzae* protein D. Other proteins, such as Human serum ovalbumin (HSA), or purified protein derivative of tuberculin (DPPD) may also be used as carrier proteins.

The amount of conjugate in each vaccine dose is preferably selected as an amount that induces an immunoprotective response without significant, adverse effects. Such an amount may vary depending upon the pneumococcal serotype. Generally, each vaccine dose comprises about 2-3 μg of each polysaccharide except 6B, which comprises about 4-5 μg, or preferably about 2.2 μg of each polysaccharide except 6B, which comprises about 4.4 μg Preferably the PCV is a 25 valent sterile liquid formulation comprising capsular polysaccharides of 25 serotypes selected from 1, 2, 3, 4, 5, 6B, 6C, 7F, 8, 9V, 9N, 10A, 11A, 12F, 14, 15 (A, B, and/or C), 16F, 17F, 18C, 19A, 19F, 20, 22F, 23B, 23F, 24F, 33F and 35B individually conjugated to carrier protein. Each 0.5 mL dose is formulated to contain: about 2 μg of each polysaccharide, except for 6B at about 4 μg; about 50-90 μg of CRM197 carrier protein; about 0.125-0.150 mg of elemental aluminum (0.5-0.625 mg aluminum phosphate) as adjuvant; and sodium chloride and L-histidine buffer.

The disclosure includes methods of inducing an immune response to a *S. pneumoniae* capsular polysaccharide conjugate, comprising administering to a human an immunologically effective amount of the multivalent immunogenic composition as disclosed herein.

The following examples illustrate embodiments of the invention, but should not be viewed as limiting the scope of the invention.

EXAMPLES

Example 1 Purification of 24F Polysaccharide, Chemical Structure Determination Using NMR Spectroscopy, HPAEC-PAD and Permethylation Followed by GC-MS Analysis Isolation and Purification of 24F Capsular Polysaccharide Cultivation of Bacteria Cultures of bacteria were conducted in a 5-10-L fermenter containing medium and conditions appropriate for each strain. The whole broth of the bioreactor was precipitated with 0.15% deoxycholate, decanted and centrifuged. Cells were separated from the culture broth by tangential microfiltration. Cell-free micro filtrate was used for CPS-purification for *S. pneumoniae* and additional strains as well.

The cell-free CPS was concentrated to 1-20-fold by tangential flow ultrafiltration (TFUF) membranes of 30-100 kDa. The concentrate was biofiltered with buffer. The water soluble-CPS fractions from serotype 24F were adjusted to pH 7. Recombinant enzymes were added successively: Benzonase (Tris-HCl 50 mM containing 2 mM $MgCl_2$ and 20 mM NaCl); Mutanolysin/Lysozyme (1:1); β-D-N-acetyl glucosaminidase; and Proteinase K were added with a 2-4 hrs interval between them and incubated for 12-24 hours at 37° C.-56° C. under alkaline pH (pH 8.8-10.5) at 50-100 rpm. Low-molecular-mass contaminants resulting from enzymatic degradation and detergent treatment were eliminated by the second TFUF membrane of 30-100 kDa cut-off. Purified CPS was sterile filtered by a 0.2μιτι membrane and stored at minus 20° C.

Further purity was achieved by wt. to residual protein, nucleic acid and endotoxin using multimodal chromatography or hydrophobic interaction or Ion-exchange chromatography steps. Multimodal chromatography was also used to remove the residual enzymes which were used during purification steps.

Monosaccharide Composition Analysis of Serotype 24F Capsular PS

Monosaccharide composition analysis of 24F PS and HF-treated 24F PS (HF-PS) were performed using HPAE-PAD composition analysis. Polysaccharide was hydrolyzed by 2M TFA at 100° C. for 4 hr.

Monosaccharide composition analysis of PS was performed using both alditol acetate and Tri-methyl silyl ether derivatization methods using GC-MS. For alditol acetate analysis 25 μg of material was hydrolyzed using 2N $CF_3COOH$ at 100° C. for 4 h followed by derivatization of the monosaccharides to corresponding alditol-acetate derivative (AA). The monosaccharides were identified using Agilent GC-MS (Agilent Technologies) equipped with Restek-5 ms column (30 m×0.25 mm×0.25 μm). The temperature gradient used for chromatography was 80° C. for 2 min followed by temperature gradient of 10° C./min to 180° C.; hold for 2 min then 2° C./min to 220° C. hold for 5 min followed by 5° C./min to 240° C. hold for 5 min. Injector and transfer line temperature was set to 220° C. and 280° C. respectively. Helium gas was used as carrier gas at a flow rate of 1.2 mL/min. The composition analysis was also performed by GC-MS as TMS derivative which showed the presence of high amount of Ribitol along with Arabinitol, Rha, Glc and GlcNAc. Samples were methanolyzed using 1M MeOH-HCl at 80° C. for 16 h followed by removal of acid, re-N-acetylation and TMS derivatization. The oven temperature gradient started at 5° C./min from 100° C. till 120° C. hold for 1 min and next ramp at 3° C./min to final temperature of 230° C. followed by 4 min hold. The injector and transfer line temperature were set at 220° C. and 280° C. respectively.

Glycosyl Linkage Analysis of 24F Capsular Polysaccharide

Figure 2A:
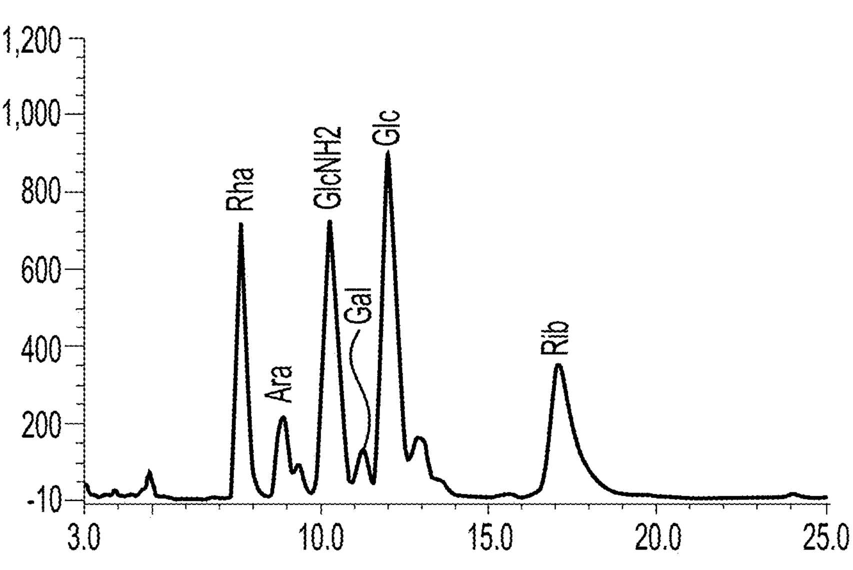
FIG. 2A Glycosyl composition analysis of serotype 24F Polysaccharide.
Figure 2B:
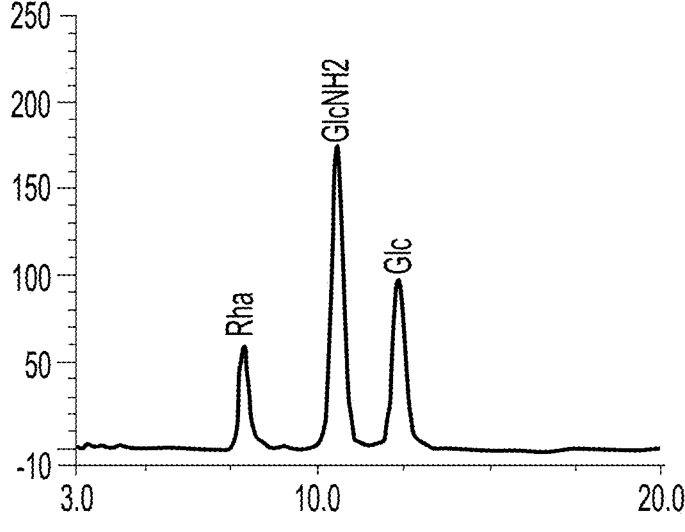
FIG. 2B Glycosyl composition analysis of HF treated 24F PS by HPAE-PAD.

Linkage analysis of PS was performed using dried PS dissolved in anhydrous DMSO, followed by addition of NaOH slurry in anhydrous DMSO and $CH_3I$. The reaction was continued for 45 min followed by quenching using ice-cold water. Per-O-methylated PS was extracted from the reaction mixture by extracting with chloroform. The chloroform layer was dried and hydrolyzed using 4N TFA at 100° C. for 4 h. The hydrolyzed samples were reduced and acetylated to give mixture of partially methylated alditol acetate derivative (PMAA) of the constituent monosaccharides. The PMAA derivatives were identified using GC-MS (Agilent it Technologies) chromatograph equipped with Restek-5 ms (30 m×0.25 mm×0.25 μm) fused-silica capillary column using a temperature gradient of 180° C.→240° C. at 2° C./min (sec FIGS. 2A and 2B).

Figure 3A:
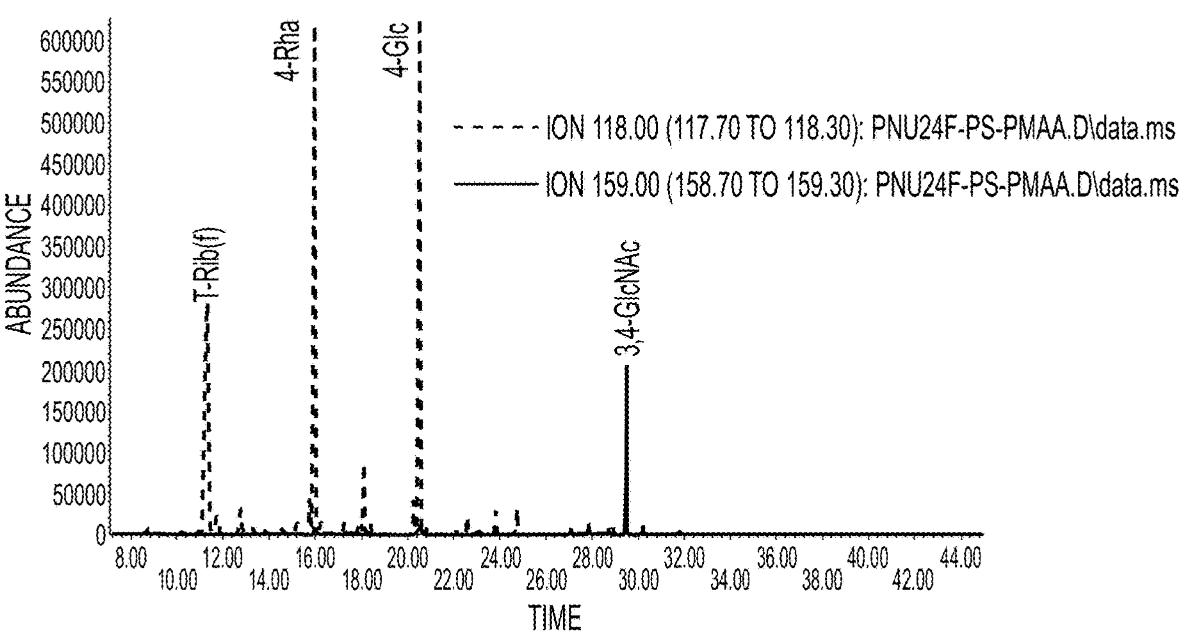
FIG. 3A Linkage analysis of PNU24F polysaccharide by GC-MS as partially methylated alditol acetate derivative.
Figure 3B:
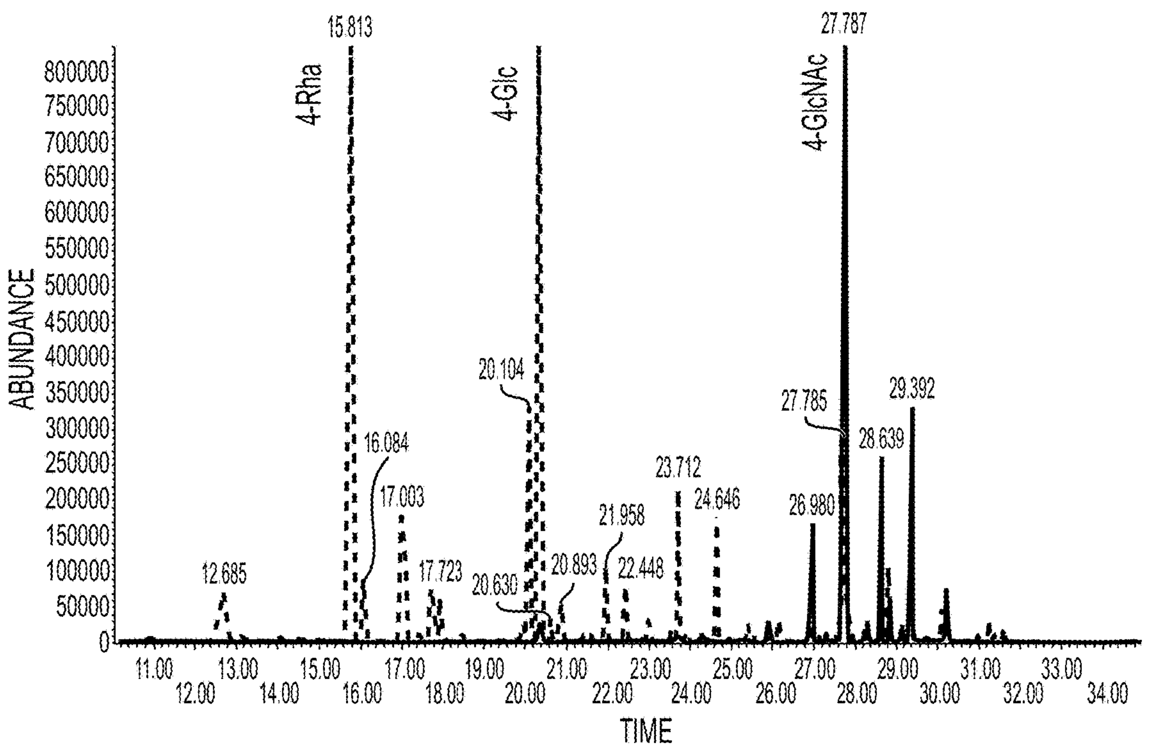
FIG. 3B Linkage analysis of HF treated PNU24F polysaccharide by GC-MS as Partially methylated alditol acetate derivative.

Another experiment of dephosphorylation of the PS (HF-PS) was performed using aqueous 48% HF treatment followed by dialysis of the sample using 1 KD MWCO dialysis tubing to remove excess HF and small molecule. The chemical composition and linkage analysis were performed using de-phosphorylated PS (HF-PS) (see FIGS. 3A and 3B).

NMR Analysis and Structure of New Serotype 24F Capsular Polysaccharide 1D and 2D NMR were performed on $D_2O$ exchanged PS using Bruker Daltroniks 600 MHz NMR using 5 mm broad band probe. The data was analyzed using Top-spin software provided by the company.

Monosaccharide composition analysis of the polysaccharide indicated the presence of Arabinitol, Rha, Rib, Glc and GlcNAc in equimolar ratio. The 1D $^1$H-proton NMR revealed the presence of several anomeric peaks and comparing the 2D $^1$H-$^{13}$C HSQC-NMR spectrum (see FIG. 4) it was clear that there were 4 distinct peaks in $^{13}$C dimension. The chemical shift values for proton NMR at δ5.1 and 4.87 ppm corresponds to α-anomers and several overlapping peaks with chemical shift values between δ4.52-4.56 ppm corresponds to β-anomers. The carbon chemical shifts for the anomeric are 94.0 ppm, 97 ppm for α-anomeric linkages and 104 and 101.5 ppm for β-anomeric linkages. Other signature peaks are several N-acetyl methyl singlets between 1.98-2.02 ppm and 6-deoxy methyl group or Rha residue at 1.16 pmm with coupling constant of 6.4 Hz. The 2D-HSQC NMR spectrum also shows that polysaccharide contained several nitrogen-bearing carbons (C-2 of GlcN) between 853 to 50 ppm and non-substituted C6-$CH_2$OH groups at δ60.4 ppm. Several CH3-C groups (C-6 of Rha) were also seen within δ20 to 16 ppm. The polysaccharide contains the major signal corresponds to a regular tetra-saccharide repeating unit with Rib(f), Rha, Glc and GlcNAc as main constituents.

The Glycosyl linkage analysis data on native PS indicated the presence of T-Arabinitol, Rib(f), 4-Rha, 4-Glc and 3/4-GlcNAc. This leads to a proposed structure with repeating unit consisting of Arabinitol, Rha, Glc, GlcNAc and Rib(f) unit. The PS was treated with aqueous 48% HF to selectively remove the phospho-di ester bonded moiety only. Composition analysis of the HF-PS showed the absence of any Ribose unit and only Rha, Glc and GlcNAc was present in the polysaccharide. Linkage analysis data on HF-PS clearly showed the absence of T-Rib(f) residue and presence of 4-Rha, 4-Glc and 4-GlcNAc as major peaks in almost 1:1:1 ratio (loss of Arabilitol suggests Phosphyrylation). This data clearly indicates that Rib(f) moiety is linked to the 3-position of GlcNAc residue via phospho-diester bond to the 3-position of GlcNAc residue (see FIG. 1). The NMR analysis of HF-PS is also on being conducted to show the structure of linear polysaccharide chain.

Example 2 Conjugation of 24F Serotype Pneumococcal Polysaccharide to Carrier Protein to Form Polysaccharide-CRM197 Conjugates Polysaccharide size reduction, activation and conjugation process for *S. pneumoniae* Serotype 24F and other serotypes, e.g., 1, 2, 3, 4, 5, 6C, 6B, 7F, 8, 9V, 9N, 10A, 11A, 12F, 14, 15 (A, B and/or C), 16F, 17F, 18C, 19A, 19F, 20, 22F, 23B, 23F, 33F and 35B.

24F Polysaccharides. 100 mg each of capsular polysaccharide (CPS) of *S. pneumoniae* 24F was dissolved in 10 ml of aqueous solution containing 10 mM of acetic acid or 0.1 M HCl at pH 2.5-3.0 and hydrolysis is carried out by maintaining the solution at a temperature of 60-85° C. for a period of 60-120 mins. The so-obtained oligosaccharides after neutralization, diafiltered using 3-10 KDa TFF Centricon filters. Polysaccharide concentration was measured using Anthrone assay and molecular size distributions (KDa) obtained are in the range of 10-50 KDa, 30-100 KDa, and 100-300 KDa.

CPS (50 mg) moiety (native polysaccharides of size between ≥200-500 KDa or size-reduced polysaccharides of size between 10-50 KDa, 30-100 KDa and 100-300 KDa) were activated cyanylation reagents used in an activation process. Polysaccharide molecular size distributions were determined using SEC-HPLC (Shodex SB-405 and SB-406 SEC columns) with analysis using (10-1000 KDa) Pollulan mixture as reference standard (Pollulan standards from Shodex, USA).

A spacer arm was introduced to CRM197 by reaction with 5-8-fold molar excess of adipic acid dihydrazide (ADH_Sigma) at pH 5.8-6.2 for 3-5 hr. Long spacer arm (bifunctional linker or long 4-arm linker) was introduced into CRM197 by reaction with 5-10-fold molar excess of at pH 5.6-6.0 for 3-5 h.

Synthesis of Pneumococcal Polysaccharide 24F Monovalent Conjugates

Differently size reduced and derivatized size reduced Polysaccharides were activated (50 mg) (native polysaccharides of size between ≥200-500 KDa or size-reduced polysaccharides of size between 10-50 KDa, 100-300 KDa, 30-100 KDa) were activated cyanylation reagents (CDAP) commonly used in activation process.

Carrier protein CRM197 was further derivatized with short chain homo-bifunctional hydrazide linker. Typical reagent was adipic acid di-hydrazide (ADH). Homo or hetero-bifunctional PEG linkers bearing di-amine, di-hydrazide, or amine or hydrazide-carboxylic acid/aldehyde functional groups, e.g., NH2-PEG(1K-3.5K)—NH2, HZ-PEG(1-3.5K)—HZ, NH2-PEG3.5K—COOH were used. Several other homo- or hetero-bifunctional spacer arms can also be used for derivatization. Short spacer arm was introduced to carrier protein CRM197 by reaction with 5-8 fold molar excess of adipic acid-dihydrazide (Sigma) at pH 5.8-6.2 in 300-600 mM MES buffer for 3-5 hr at RT. Long chain linker (bifunctional linker or long tetra functional linker was introduced into carrier protein by reaction with 5-10-fold molar excess of the linker to the oligosaccharide at pH 5.8-6.2 in 300-600 mM MES buffer for 3-5 hr at RT (room temperature).

Separate aliquots of same or differently size reduced and derivatized size reduced Polysaccharides (10 mg/ml) (with short spacer arm ADH and long spacer arm HZ-PEG-HZ) were mixed with 1 ml aliquot of the derivatized CRM197 protein sample (10 mg/ml) at 4° C. for 8-12 hrs in presence of EDC/sNHS. The conjugates containing both long and short chain linkers were purified using 100-300 KDa centricon filters (EMD Millipore). Each monovalent conjugate was assayed for total polysaccharide content by either anthrone or uronic acid assay, total protein content by BCA or Lowry assay. The conjugates containing both long and short chain linkers were purified using 100-300 KDa centricon filters (EMD Millipore). Each monovalent conjugate was assayed for total polysaccharide content by either anthrone or uronic acid assay, total protein content by BCA or Lowry assay.

Example 3 Formulation of 25-Valent Conjugates Containing Serotypes 24F

Investigational Formulation of 25V- or Higher Valent Pneumococcal Conjugate Vaccine. Pneumococcal polysaccharide-CRM197 conjugates for serotypes containing 24F as well as other polysaccharides such as serotypes 1, 2, 3, 4, 5, 6B, 6C, 7F, 8, 9V, 9N, 10A, 11A, 11F, 12F, 14, 15 (A, B and/or C), 16F, 17F, 18C, 19A, 19F, 20, 22F, 23B, 23F, 33F, and 35B were combined to yield final antigen concentration of 4.0 μg PS/mL. Sodium chloride (150 mM) solution, 10-20 mM histidine, and 0.001% Tween-20 was also used during the formulation process as diluent, and aluminum phosphate (Adju-Phos, Brenntag, USA) was used as investigational adjuvant. 24-V or more conjugate was aseptically filled in 2 mL sterile vials. PNEUMOVAX® (Merck, USA) or PREVNAR-13® (Pfizer, USA) was used as two control commercial vaccine formulation.

Example 4 Animal Immunogenicity Study of a 25-Valent Conjugates Containing Serotypes 24F (Total IgG) Using Bead Based Multiplex ELISA Immunogenicity Studies of the Conjugates A New Zealand white rabbit model (NZW) was selected in this work to compare the immunogenicity of the Pneumococcal PS-CRM197 conjugates. Rabbits from all groups (18 or higher-Valent conjugates, PREVNAR-13®, Pfizer and PNEUMOVAX®-23 (Merck USA) were examined for serological titers before and after immunization periods. For all groups, pre-immunization, booster dose (7 and 14-days) and terminal bleed (28 days) were collected and aliquoted and store at −80° C. until use. Immunogenicity assay for the determination of Total IgG were performed according to the standard protocol using reference standard serum 007 (CBER, FDA, USA). Reference serum and rabbit serum were diluted and pre-adsorbed for cross-reacting antibodies by treatment with Pneumococcal CWPS and non-vaccine serotype 25 PS. Human/rabbit/mouse monoclonal anti-polysaccharide antibodies were used for total IgG estimation. Bio-Plex 200 (Bio-Rad) reader were used as per the manufacturer's instructions.

Figures 4, 5:
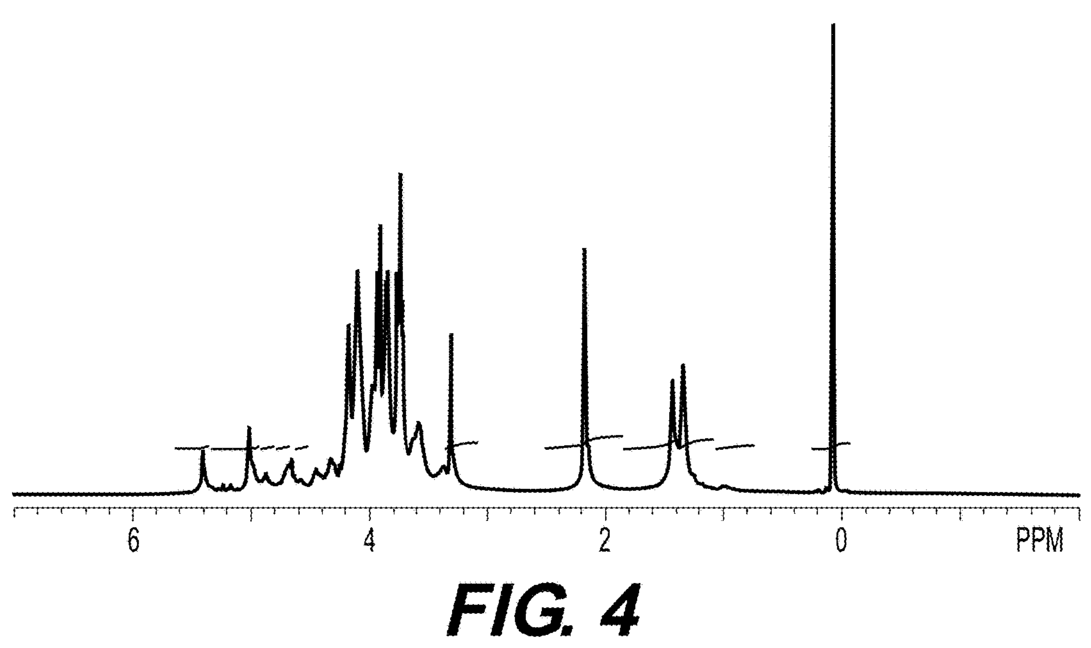
FIG. 4 $^1$H NMR spectroscopy of 24F capsular polysaccharide compared to SSI 24F capsular polysaccharide.
FIG. 5 Total IgG 25-V conjugate vaccine which includes serotype 24F conjugate IgG μg/ml, 007SP as reference serum.

Immunogenicity of the conjugates, i.e. capsular polysaccharide specific antibodies (total IgG) were measured using bead-based ELISA assay method were given in FIG. 5. Total IgG values were compared head-to-head with PREVNAR-13® in rabbit immunogenicity data. 28-day data shows significant increase in titer in IVT-24F conjugate as well for other serotypes conjugates vaccine compared to PREVNAR-13® vaccine.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. The term comprising, wherever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. A method of manufacture of an immunogenic composition containing at least 25 capsular polysaccharides of *Streptococcus pneumonia* comprising *Streptococcus pneumonia* capsular polysaccharides of serotypes 1, 2, 3, 4, 5, 6B, 6C, 7F, 8, 9N, 9V, 10A, 12F, 14, 15A, 15B, 16F, 18C, 19A, 19F, 22F, 23F, 24F, 33F and 35B, activating the at least 25 capsular polysaccharides;

conjugating the activated capsular polysaccharides directly or indirectly through linkers to carrier proteins; and isolating the immunogenic composition, wherein the 24F serotype capsular polysaccharide comprises a repeating unit of the chemical structure:

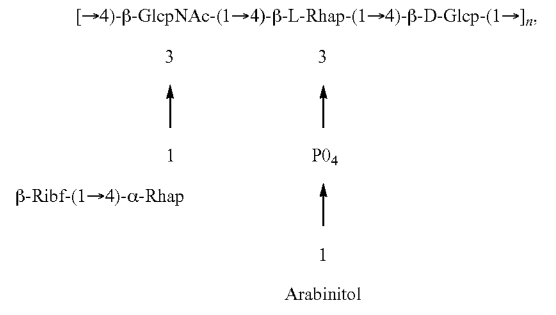

and wherein the at least 25 capsular polysaccharides are conjugated to one or more carrier proteins, and at least one conjugation is through a bi-functional or a multifunctional spacer/linker.

2. The method of claim 1, wherein the isolated immunogenic composition is subjected to multimodal chromatography to remove endotoxin.

3. The method of claim 1, wherein the isolating comprises diafiltration of the individual conjugates followed by filter sterilization.

4. The method of claim 1, wherein the immunogenic composition manufactured further comprises capsular polysaccharides of *S. pneumonia* serotypes 11A, 15C, I7F, 20 and/or 23B.

5. The method of claim 1, wherein the immunogenic composition manufactured comprises 25 capsular polysaccharides of *S. pneumonia* serotypes.

6. The method of claim 1, wherein the immunogenic composition manufactured comprises 26 capsular polysaccharides of *S. pneumonia* serotypes.

7. The method of claim 1, wherein the immunogenic composition manufactured comprises 27 capsular polysaccharides of *S. pneumonia* serotypes.

8. The method of claim 1, wherein the immunogenic composition manufactured comprises 28 capsular polysaccharides of *S. pneumonia* serotypes.

9. The method of claim 1, wherein the immunogenic composition manufactured comprises 29 capsular polysaccharides of *S. pneumonia* serotypes.

10. The method of claim 1, wherein the immunogenic composition manufactured comprises 30 capsular polysaccharides of *S. pneumonia* serotypes.

11. The method of claim 1, wherein the one or more carrier proteins are selected from the group consisting of native or recombinant cross-reactive material (CRM) or domain of CRM, CRM197, tetanus toxin, tetanus toxin heavy chain proteins, diphtheria toxoid, tetanus toxoid, *Pseudomonas* exoprotein A, *Pseudomonas aeruginosa* toxoid, *Bordetella pertusis* toxoid, *Clostridium perfringens* toxoid, *Escherichia coli* heat-labile toxin B subunit, *Neisseria meningitidis* outer membrane complex, *Hemophilus influenzae* protein D, Flagellin Fli C, Horseshoe crab Haemocyanin, and fragments, derivatives, and modifications thereof.

12. The method of claim 1, wherein each of the at least 25 capsular polysaccharides of the immunogenic composition manufactured are conjugated to two or more carrier proteins through the bi-functional or the multifunctional spacer/linker.

13. The method of claim 1, wherein the immunogenic composition manufactured further comprises a pharmaceutically acceptable carrier.

14. The method of claim 13, wherein the pharmaceutically acceptable carrier comprises oil, water, water-in-oil or oil-in-water mixtures, an alcohol, a buffer, a mono-, di- or polysaccharide, a sugar alcohol, a glycerol, an amino acid, histidine, arginine, a preservative, a stabilizer, polysorbate, or a combination thereof.

15. The method of claim 1, wherein the immunogenic composition manufactured further comprises an adjuvant.

16. The method of claim 15, wherein the adjuvant comprises aluminum salt, calcium phosphate, a liposome of monophosphoryl lipid A (MPLA), saponin QS-21, a TLR7/8 agonist, and derivatives and combinations thereof.

17. The method of claim 1, wherein the immunogenic composition manufactured is a vaccine.

18. The method of claim 17, wherein the amount of polysaccharide from each of the serotypes comprises about 2-5 μg per dose of vaccine.

19. The method of claim 17, wherein the total amount of polysaccharide of the immunogenic composition manufactured comprises about 60-70 μg per dose of vaccine.

20. The method of claim 17, wherein the total amount of polysaccharide of the immunogenic composition manufactured comprises about 50-90 μg per dose of vaccine.

21. A method of manufacture of an immunogenic composition containing at least 25 capsular polysaccharides of *Streptococcus pneumonia* comprising *Streptococcus pneumonia* capsular polysaccharides of serotypes 1, 2, 3, 4, 5, 6B, 6C, 7F, 8, 9N, 9V, 10A, 12F, 14, 15A, 15B, 16F, 18C, 19A, 19F, 22F, 23F, 24F, 33F and 35B, activating the at least 25 capsular polysaccharides;

conjugating the activated capsular polysaccharides directly or indirectly through linkers to carrier proteins;

isolating individual conjugates by diafiltration;

sterilizing individual conjugates; and collecting the sterilized individual conjugates as the immunogenic composition, wherein the 24F serotype capsular polysaccharide comprises a repeating unit of the chemical structure:

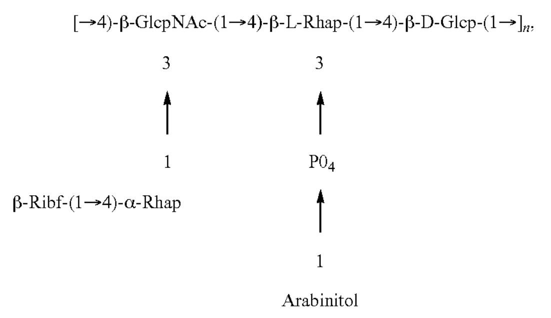

and wherein the at least 25 capsular polysaccharides are conjugated to one or more carrier proteins, and at least one conjugation is through a bi-functional or a multifunctional spacer/linker.

22. The method of claim 21, wherein sterilizing is by filter sterilization.

23. The method of claim 21, wherein the immunogenic composition is subjected to multimodal chromatography to remove endotoxin.

24. The method of claim 21, wherein the immunogenic composition manufactured further comprises capsular polysaccharides of *S. pneumonia* serotypes 11A, 15C, I7F, 20 and/or 23B.

25. The method of claim 21, wherein the immunogenic composition manufactured comprises 25 capsular polysaccharides of *S. pneumonia* serotypes.

26. The method of claim 21, wherein the immunogenic composition manufactured comprises 26 capsular polysaccharides of *S. pneumonia* serotypes.

27. The method of claim 21, wherein the immunogenic composition manufactured comprises 27 capsular polysaccharides of *S. pneumonia* serotypes.

28. The method of claim 21, wherein the immunogenic composition manufactured comprises 28 capsular polysaccharides of *S. pneumonia* serotypes.

29. The method of claim 21, wherein the immunogenic composition manufactured comprises 29 capsular polysaccharides of *S. pneumonia* serotypes.

30. The method of claim 21, wherein the immunogenic composition manufactured comprises 30 capsular polysaccharides of *S. pneumonia* serotypes.

31. The method of claim 21, wherein the one or more carrier proteins are selected from the group consisting of native or recombinant cross-reactive material (CRM) or domain of CRM, CRM197, tetanus toxin, tetanus toxin heavy chain proteins, diphtheria toxoid, tetanus toxoid, *Pseudomonas* exoprotein A, *Pseudomonas aeruginosa* toxoid, *Bordetella pertusis* toxoid, *Clostridium perfringens* toxoid, *Escherichia coli* heat-labile toxin B subunit, *Neisseria meningitidis* outer membrane complex, *Hemophilus influenzae* protein D, Flagellin Fli C, Horseshoe crab Haemocyanin, and fragments, derivatives, and modifications thereof.

32. The method of claim 21, wherein each of the at least 25 capsular polysaccharides of the immunogenic composition manufactured are conjugated to two or more carrier proteins through the bi-functional or the multifunctional spacer/linker.

33. The method of claim 21, wherein the immunogenic composition manufactured further comprises a pharmaceutically acceptable carrier.

34. The method of claim 33, wherein the pharmaceutically acceptable carrier comprises oil, water, water-in-oil or oil-in-water mixtures, an alcohol, a buffer, a mono-, di- or polysaccharide, a sugar alcohol, a glycerol, an amino acid, histidine, arginine, a preservative, a stabilizer, polysorbate, or a combination thereof.

35. The method of claim 21, wherein the immunogenic composition manufactured further comprises an adjuvant.

36. The method of claim 35, wherein the adjuvant comprises aluminum salt, calcium phosphate, a liposome of monophosphoryl lipid A (MPLA), saponin QS-21, a TLR7/8 agonist, and derivatives and combinations thereof.

37. The method of claim 21, wherein the immunogenic composition manufactured is a vaccine.

38. The method of claim 37, wherein the amount of polysaccharide from each of the serotypes comprises about 2-5 μg per dose of vaccine.

39. The method of claim 37, wherein the total amount of polysaccharide of the immunogenic composition manufactured comprises about 60-70 μg per dose of vaccine.

40. The method of claim 37, wherein the total amount of polysaccharide of the immunogenic composition manufactured comprises about 50-90 μg per dose of vaccine.

* * * * *